US006596505B2

(12) United States Patent (10) Patent No.: US 6,596,505 B2
Ceri et al. (45) Date of Patent: Jul. 22, 2003

(54) APPARATUS AND METHODS FOR TESTING EFFECTS OF MATERIALS AND SURFACE COATINGS ON THE FORMATION OF BIOFILMS

(75) Inventors: Howard Ceri, Calgary (CA); Merle Edwin Olson, Calgary (CA)

(73) Assignee: University Technologies International, Inc. (CA)

( * ) Notice: Subject to any disclaimer, the term of this patent is extended or adjusted under 35 U.S.C. 154(b) by 0 days.

(21) Appl. No.: 09/835,562

(22) Filed: Apr. 17, 2001

(65) Prior Publication Data

US 2001/0049975 A1 Dec. 13, 2001

Related U.S. Application Data

(60) Provisional application No. 60/198,083, filed on Apr. 17, 2000.

(51) Int. Cl.[7] .............................. C12Q 1/02; C12Q 1/00; C12M 1/00

(52) U.S. Cl. ........................... 435/29; 435/283.1; 435/4

(58) Field of Search ............................... 435/29, 283.1, 435/34, 4

(56) References Cited

U.S. PATENT DOCUMENTS

| | | | |
|---|---|---|---|
| 2,956,931 A | 10/1960 | Goldberg | 435/29 |
| 3,455,788 A | 7/1969 | Curry et al. | 435/29 |
| 3,691,988 A | 9/1972 | Clarke | 435/29 |
| 3,745,091 A | 7/1973 | McCormick | |
| 4,115,200 A | 9/1978 | Anderson | 435/29 |
| 4,432,642 A | 2/1984 | Tolles | |
| 4,483,925 A | 11/1984 | Noack | 435/29 |

(List continued on next page.)

FOREIGN PATENT DOCUMENTS

| | | |
|---|---|---|
| CA | 1 075 571 | 4/1980 |
| DE | 1 812 419 | 6/1970 |
| EP | 0 709 678 A1 | 5/1996 |
| FR | 1.221.896 | 6/1960 |
| FR | 1245035 | 9/1971 |
| FR | 1 522 128 | 8/1978 |
| FR | 2 548 685 | 1/1985 |
| FR | 2 739 448 | 4/1997 |
| JP | 9043229 A | 2/1997 |
| WO | WO 83/03677 | 10/1983 |
| WO | WO 94/10838 | 5/1994 |
| WO | WO 95/27039 | 10/1995 |
| WO | WO 97/33972 | 9/1997 |

OTHER PUBLICATIONS

McCoy, et al., "Observations of fouling biofilm formation", Canadian Journal of Microbiology, vol. 27, Issue 9, pp. 910–917 (Sep. 1981).

(List continued on next page.)

Primary Examiner—Louise N. Leary
(74) Attorney, Agent, or Firm—Burns, Doane, Swecker & Mathis, L.L.P.

(57) ABSTRACT

The present invention relates to an apparatus and methods for testing the formation of biofilms on various materials. The apparatus includes a lid and a vessel, wherein the lid may be configured to accept various materials for the testing of biofilm formation. For example, the lid may contain a plurality of projections onto which materials may be coated or disposed. The vessel is adapted to receive the lid in a fluid tight communication and to retain a liquid growth medium therein. After a material has been disposed upon the projections, the material is suspended within the vessel containing the liquid growth medium. The material is allowed to incubate for a period of time in which a biofilm forms upon the material. The material is then removed from the liquid growth medium and the biofilms formed thereupon are used to test the efficiency of various biocides.

76 Claims, 7 Drawing Sheets

U.S. PATENT DOCUMENTS

| | | | |
|---|---|---|---|
| 5,017,342 A | 5/1991 | Haberzettl et al. ............ 435/29 | |
| 5,160,378 A | 11/1992 | Tuunanen et al. | |
| 5,217,493 A | 6/1993 | Raad et al. .................... 435/29 | |
| 5,312,813 A | 5/1994 | Costerton et al. ............. 435/29 | |
| 5,326,533 A | 7/1994 | Lee et al. ..................... 435/29 | |
| 5,349,874 A | 9/1994 | Schapira et al. .............. 435/29 | |
| 5,462,644 A | 10/1995 | Woodson ..................... 435/29 | |
| 5,605,836 A | 2/1997 | Chen et al. .................... 435/29 | |
| 5,861,306 A | 1/1999 | Pugh et al. | |
| 5,928,889 A | * 7/1999 | Bakich et al. ................ 435/29 | |
| 5,981,272 A | 11/1999 | Chang | |
| 6,051,423 A | * 4/2000 | Ceri et al. ............... 435/288.3 | |
| 6,306,646 B1 | 10/2001 | Saad et al. | |
| 6,326,190 B1 | 12/2001 | Ceri et al. | |
| 6,410,256 B1 | * 6/2002 | Ceri et al. ..................... 435/29 | |

OTHER PUBLICATIONS

Morck, et al., "Therapeutic Efficacy of Fleroxacin for Eliminating Catheter–Associated Urinary Tract Infection in a Rabbit Model", The American Journal of Medicine, vol. 94 (suppl. 3A), pp. 3A–23S –3A30S (Mar. 22, 1993).

Gjaltema, et al., "Heterogeneity of Biofilms in Rotating Annular Reactors: Occurance, Structure, and Consequences", Biotechnology and Bioengineering, vol. 44, pp. 194–204 (1994).

Patel, et al., "Susceptibilty of Biofilms of Streptococcus sanguis to chlorhexidine gluconate and cetylpyridinium chloride", Oral Microbiology and Immunology, vol. 11, 2 pages (1996).

Darouiche, et al., "Vancomycin Penetration into Biofilm Covering Infected Prostheses and Effect on Bacteria", The Journal of Infectious Diseases, vol. 170, pp. 720–723 (1994).

Olson, et al., "Amdinocillan Treatment of Catheter–Associated Bacteriuria in Rabbits", The Journal of Infectious Diseases, vol. 159, pp. 1065–1072 (Jun. 1989).

Miyake, et al., "Simple Method for Measuring the Antibiotic Concentration Required to Kill Adherent Bacteria", Chemotherapy, vol. 38, pp. 286–290 (1992).

Morek, et al., "Comparative evaluation of fleroxacin, ampicillin, trimethoprimsulfamethozazole, and gentamicin as treatment of catheter–associated urinary tract infection in a rabbit model", International Journal of Antimicrobial Agents, vol. 4, pp. S21–S27 (1994).

Casterton, et al., "Microbial Biofilms", Annual Reviews Microbial, vol. 49, pp. 711–743 (1995).

Prosser, "Method of Evaluating Effects of Antiobiotics on Bacterial Biofilm", Antimicrobial Agents and Chemotherapy, vol. 31, No. 10, pp. 1502–1506 (1987).

Olsen, et al., "Evaluation of strategies for central venous catheter replacement", Critical Care Medicine, vol. 22, No. 6, pp. 797–804 (1992).

Richards, et al., "An assay of Staphylococcus epidermidis biofilm responses to therapeutic agents", The International Journal of Artificial Organs, vol. 15, No. 11, pp. 777–787 (1993).

Johnston, et al., "Disinfection tests with intact biofilms: combined use of the Modified Robbins Device with impedance detection", Journal of Microbiological Methods, vol. 21, pp. 15–26 (1995).

Evans, et al., "Susceptibility of bacterial biofilms to tobramyciin: role of specific growth rate and phase in the division cycle", Journal of Antimicrobial Chemotherapy, vol. 25, pp. 585–591 (1990).

Hussain, et al., "Radiochemical assay to measure the biofilm produced by coagulase–negative staphylococci on solid surfaces and its use to quantitate the effects of various antibacterial compounds on the formation of the biofilm", J. Med. Microbial, vol. 37, pp. 62–69 (1992).

Bower, et al., "Influences on the antimicrobial activity of surface–adsorbed nisin", Journal of Industrial Microbiology, vol. 15, pp. 227–233 (1995).

Ichimiya, et al., "The Influence of Azithromycin on the Biofilm Formation of Psuedomonas aeruginosa in vitro", Chemotherapy, vol. 42, pp. 186–191 (1996).

Zimmerli, et al., "Microbiological tests to predict treatment outcome in experimental device–related infections due to Staphylococcus aureus", Journal of Antimicrobial Chemotherapy, vol. 33, pp. 959–967 (1994).

Shigeta, et al., "Permeation of Antimicrobial Agents through Pseudomonas aeruginosa Biofilms: A Simple Method", Chemotherapy, vol. 43, pp. 340–345 (1997).

Ichimiya, et al., "In–vitro effects of antimicrobial agents on Pseudomonas aeruginosa biofilm formation", Journal of Antimicrobial Chemotherapy, vol. 34, pp. 331–341 (1994).

Richards, et al., "An assay to measure antibiotic efficacy against Staphylococus epidermidis Biofilms on Implant Surfaces", ASAIO Journal, pp. M570–M571 (1994).

Costerton, et al., "Mechanism of Electrical Enhancement of Efficacy of Antibiotics in Killing Biofilm Bacteria", Antimicrobial Agents and Chemotherapy, vol. 38, No. 12, pp. 2803–2804, (Dec. 1994).

Oie, et al., "Efficacy of disinfectants against biofilms cells of methicillin–resistant Staphylococcus aureus", Microbios, vol. 85, pp. 223–225 (1996).

Becton Dickinson Labware, "Innovative Products for Cell Science Research", 41 pages (no date).

Nunc, "Welcome to Nunc", Nunc Inter Med, 48 pages (Oct. 1990).

* cited by examiner

APPARATUS AND METHODS FOR TESTING EFFECTS OF MATERIALS AND SURFACE COATINGS ON THE FORMATION OF BIOFILMS

CLAIM OF PRIORITY

This application claims priority under 35 U.S.C. §119(e) to U.S. Provisional Application No. 60/198,083 filed Apr. 17, 2000, abandoned, which is incorporated herein by reference in its entirety.

FIELD OF THE INVENTION

The present invention relates to the formation of biofilms, more particularly the present invention provides apparatuses for forming biofilms on various surfaces as well as methods for testing the effects of antimicrobial agents on the formation of biofilms.

DESCRIPTION OF THE RELATED ART

Extensive study into the growth properties of bacteria in recent years has shown that bacteria form complex layers that adhere to surfaces. These complex forms of bacteria are known as biofilms, or sessile bacteria. Biofilms may cause problems in a variety of areas including the bodies of humans and animals, food processing, health care facilities and many other industries.

It is now known widely that bacteria in the form of biofilms are more resistant to antimicrobial reagents than planktonic bacteria. Yet traditional testing of antimicrobial reagents is performed utilizing planktonic bacterial. Thus, bacterial inhibitory concentration of antimicrobial reagent may be underestimated, with the result that the wrong antimicrobial reagent or wrong amount of antimicrobial reagent may be used for the treatment of bacteria.

One type of device for monitoring biofilm buildup is described in the Canadian Journal of Microbiology (1981), Volume 27, pages 910–927, in which McCoy et al. describes the use of a so-called Robins device. The Robins device includes a tube through which water in a recycling circuit can flow. The tube has a plurality of ports within the tube wall, each port being provided with a removable stud, the stud having a biofoulable surface and being capable of being retained within the port in a fixed relationship with respect to the tube so that the biofoulable surface forms part of the internal surface of the tube. Each of the studs may be removed from the ports after a desired time interval and the surfaces analyzed for the growth of microorganisms. Alternatively, any surface growth may be removed and studied independent of the stud. The number of microorganism can be estimated for instance by physical or chemical means, e.g. by detection of bacterial ATP or by further culturing the microorganisms and analyzing the products.

Referring now to U.S. Pat. No. 5,349,874, Schapira, et al. there is shown another device for biofilm growth. Bacterial growth is determined in a water carry conduit by providing a plurality of removable studs disposed within the conduit, or in a second conduit parallel to the first. The studs may be removed for analysis of biofilm growth on the studs. Such devices that utilize removable studs in a single conduit result in rather lengthy processing times and do not provide for rapid response times for testing of several different antimicrobial reagents.

In still another device which is described in *Simple Method for Measuring the Antibiotic Concentration Required to Kill Adherent Bacteria,* Miyake et al., Chemotherapy 1992; 38, 286–290, staphylococcus aureus cells adhered to the bottom of a 96 well plastic tissue culture plate were treated with serially diluted antibiotic solutions, viability of the cells were judged by their growth after a further 24 hours incubation. This method has the disadvantage of inconsistent colonization of sessile bacteria and settling of planktonic bacteria.

It would be desirable to provide an apparatus and method for testing the effects of materials, such as surface coatings, on biofilm growth. In addition, it would be desirable to provide an apparatus and method for testing the effects of materials on biofilm growth which provides rapid response times and the ability to test multiple materials or antimicrobial reagents at once.

SUMMARY OF THE INVENTION

In one aspect of the invention, there is provided a method for growing a plurality of biofilms. The method includes proving a plurality of biofilm adherent sites, the biofilm adherent sites further including a surface material, wherein the surface material models a surface likely to be involved in biofilm formation. A liquid growth medium is arranged to flow across the biofilm adherent sites, and bacteria is incubated in the presence of the liquid growth medium.

In another aspect of the invention, there is provided a method for testing biofilm growth on surface coatings in a controlled environment. The method includes, providing a plurality of biofilm adherent sites, coating the biofilm adherent sites with a material which acts as a model for a surface likely to be involved in biofilm formation, providing a liquid growth medium arranged to flow across the biofilm adherent sites, agitating the liquid growth medium to flow across the biofilm adherent sites and growing bacteria on the biofilm adherent sites.

In another aspect of the present invention, there is provided an apparatus for testing the growth of biofilms. The apparatus includes a first body having first and second surfaces, a second body having sides and a bottom defining a vessel, the second body adapted to receive the first body. The first body further including projections extending from the first surface, wherein the projections are adapted to receive a material for biofilm growth. The vessel further capable of receiving fluid in a plurality of depressions and including a means to flow the liquid within the vessel about the members.

In yet another aspect of the present invention, there is provided a method for testing the formation of biofilm growth on a material or surface coating. The method includes partially covering a plurality of projections in a testing apparatus with a material to be tested for biofilm formation. Placing the projections into a first vessel containing at least one well, wherein the well includes a liquid growth medium and a biofilm forming organism, and removing the projections from the first vessel and placing the projections into a second vessel, wherein the second vessel contains a second medium.

BRIEF DESCRIPTION OF THE DRAWINGS

There will now be described preferred embodiments of the invention with reference to the drawings, by way of illustration, in which like numerals denote like elements and in which.

DESCRIPTION OF THE EXEMPLARY PREFERRED EMBODIMENTS

The present invention relates to an apparatus and methods for testing the formation of biofilms on various materials. The apparatus includes a lid and a vessel, wherein the lid may be configured to accept various materials for testing biofilm formation. For example, the lid may contain a plurality of projections onto which materials may be coated or disposed. Alternatively, the material may be fixedly attached to the lid utilizing a biocompatible adhesive or other method of attachment. The vessel is adapted to receive the lid in a fluid tight communication and to retain a liquid growth medium therein.

After a material has been disposed upon the projections, the material is suspended within the vessel containing the liquid growth medium. The material is allowed to incubate for a period of time in which a biofilm forms upon the material. During incubation, biofilm formation may be promoted by providing a means for causing the liquid growth medium to flow across the material. After formation of a biofilm, the lid is removed from the vessel. A second vessel may be prepared in which biocides are placed into the vessel. The lid is then placed onto the second vessel and the effectiveness of the biocides may be tested.

Figure 1:
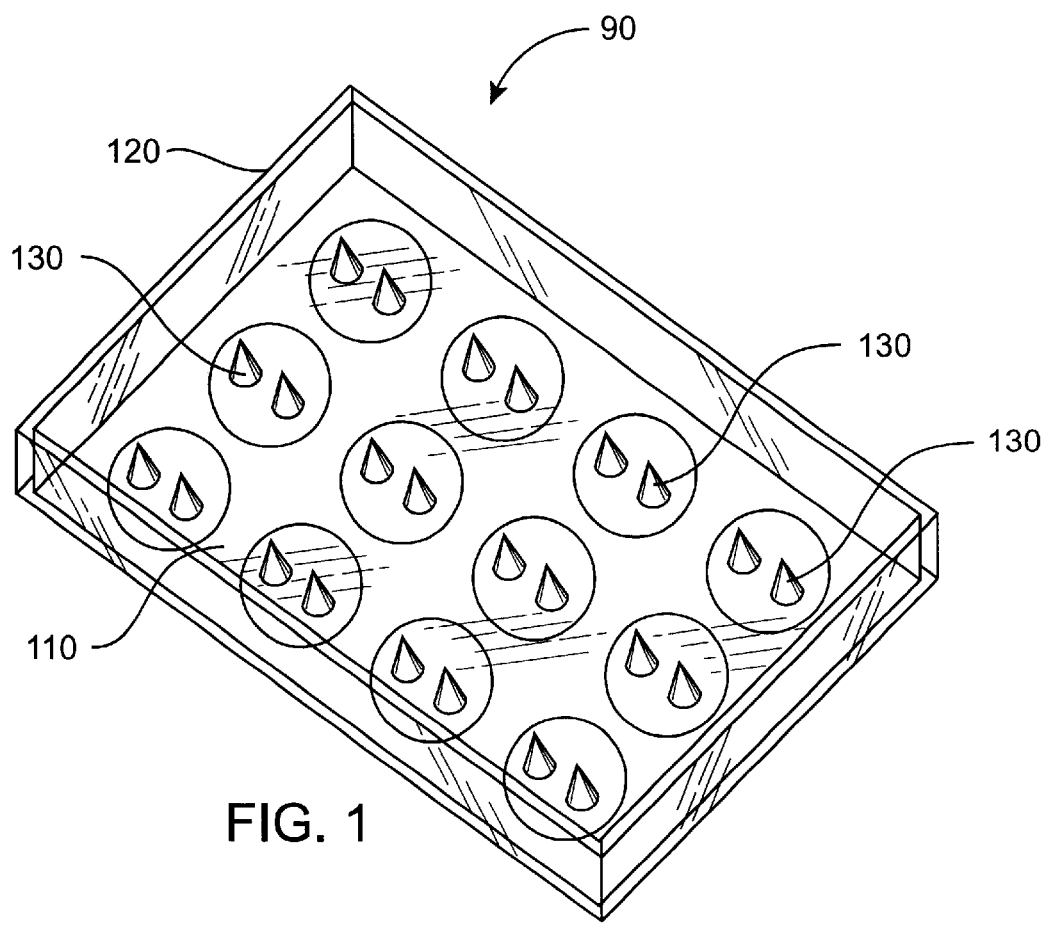
FIG. 1 is an isometric view of the lid of the present invention.

Referring now to the FIG. 1, there is shown a perspective view of a lid 90 of a biofilm growing apparatus of the present invention. As shown in FIG. 1, the lid 90 includes a plate 100 having a first surface 110, a second surface 111 (not shown), sides 120, and a plurality of projections 130 extending from the first surface 110.

Figure 2:
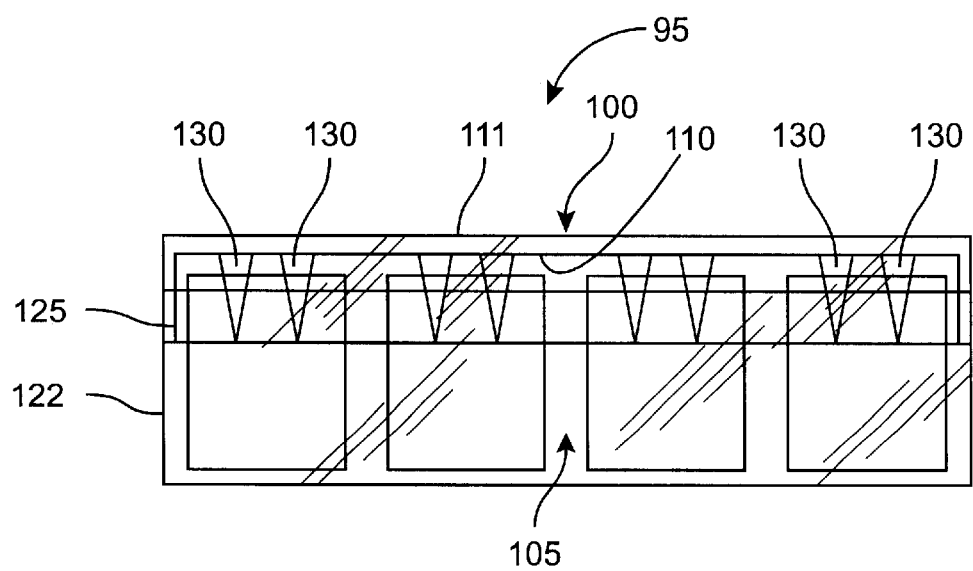
FIG. 2 is a side view of the present invention showing the lid disposed upon a vessel thereby forming an assembly.

The lid 90 may be constructed of any bio-compatible material such as stainless steel, titanium, polystyrene, urethane, or low density polyethylene (LDPE). The sides 120 extend from the plate 100 and are adapted to be received by a vessel 105, as shown in FIG. 2, to form an assembly 95 having a fluid tight seal between the lid 90 and the vessel 105.

Referring now to FIG. 1, there is shown a bottom perspective view of the lid 90. The projections 130 extend from the first surface 110 of the plate 100 and have a general conical geometry. Although shown as having general conical geometry, the projections 130 may be formed having any appropriate geometry, for example, hollow cylindrical shape, solid cylindrical or square shape or any similar geometries. The projections 130 may be formed in a number of different geometrical patterns. For example, the lid 90 may be formed having 5 rows wherein each row contains 10 projections. In a preferred embodiment the lid 90 is formed in at least three rows including at least eight projections per row.

The projections 130 are preferably unitarily formed with the plate 100 of the lid 90. Alternatively, the projections 130 may be formed by fixedly attaching an end of the projection 130 to the first surface 110 of the plate 100. Still further, the projections 130 may be formed by forming a plurality of apertures (not shown) through the first and second surfaces of plate 100 and disposing the projections 130 therethrough and affixing the projections 130 to the plate 100 with a suitable bio-compatible glue, sonic-welding, or other bio-compatible process. The projections are arranged on the first surface 110 of the lid 90 whereby two projections are arranged such that when the lid 90 is placed upon the vessel 105 two projections 130 are disposed within each well respectively. The projections are approximately between 1 cm and 3 cm in length and about 2 millimeters wide at a widest 15 point.

Figure 3:
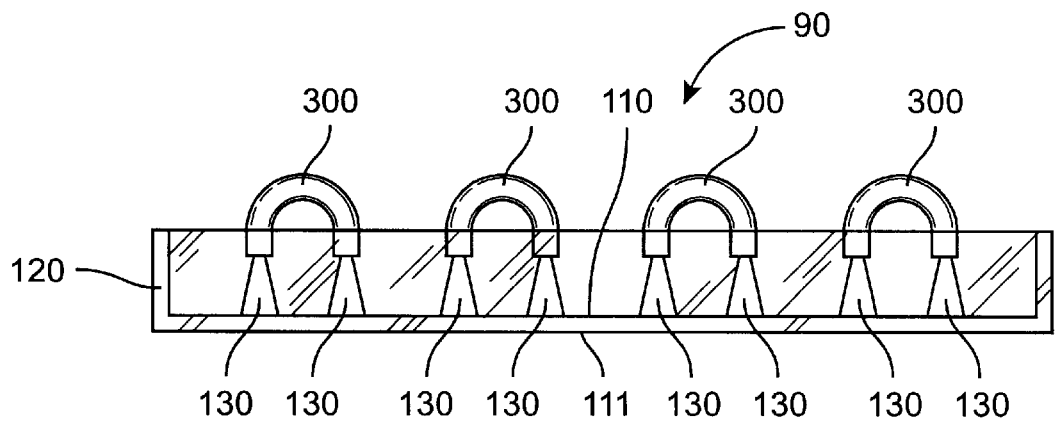
FIG. 3 is a side view of the lid of the present invention showing a biofilm growing material disposed between the projections.
Figure 4:
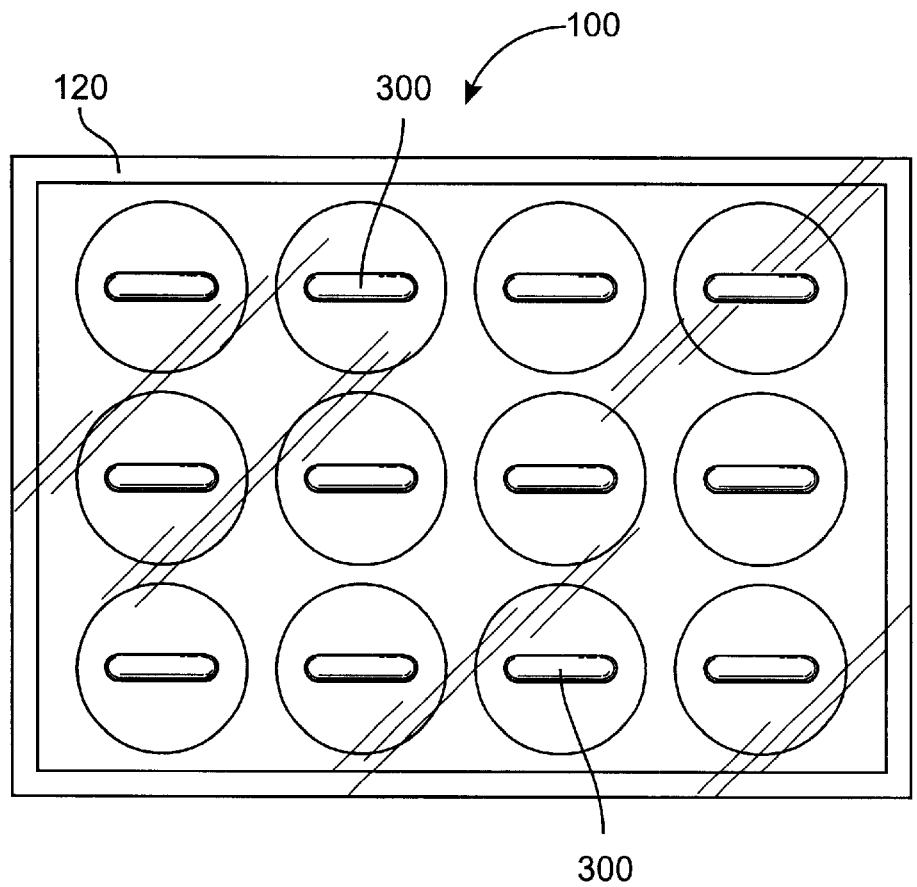
FIG. 4 is a bottom view of the lid of the invention showing a biofilm growing material disposed between the projections.

Referring now to FIGS. 3 and 4, there is shown the lid 90 of the present invention having a material 300 disposed upon and between the projections 130. Referring now to FIG. 3, there is shown a side view of the lid 90 including the projections 130 wherein the material 300 is disposed between the projections 130. The material 300 may be tubing, such as a catheter that would be utilized in a medical procedure. A catheter 300 may be prepared by cutting it into small sections having a length of about 3.5 cm. One end of the catheter 300 is placed onto one projection 130 and the other end of the catheter is placed onto another adjacent projection 130, whereby the catheter forms and arch between the first projection and a second projection as shown in FIG. 3.

An advantage of the arrangement as shown in FIGS. 3 and 4 is that the various materials 300 being tested for the growth of biofilm are tested in a manner that resembles how they would be used in vitro. Furthermore, by placing a material 300 on the projections 130 in this manner, the cut ends 301 of the material 300 are not in contact with the liquid growth medium disposed within the wells of the vessel 105. It was found that it is undesirable to expose the cut ends of the catheter to the liquid growth medium disposed in the vessel 105 because the cut ends of the catheter were not coated with the coating to be tested. It was also determined, that the liquid growth medium would 'wick' into the inner, un-coated surface of the catheter if the cut ends were in contact with the liquid growth medium. Thus, as a result it was found to be difficult to determine the formation of the biofilm on the coated portion because of the large un-coated surface in contact with the liquid growth medium. Therefore, in a preferred embodiment, the cut ends or un-coated surfaces of the material to be tested are disposed within the assembly 95 so that they are not in contact with the liquid growth medium.

The lid 90 of the present invention allows for various materials to be simultaneously tested or removed from a vessel containing a liquid growth medium. As a result, minimal handling is required during the process. Using any of the prior art systems described above requires that each individual pin be inserted and removed, therefore it is difficult to control the overall exposure time of each of the pins in the experiment. For example, it may be desirable to test the formation of biofilm on a plurality of pins, in order to do so, each of the pins (i.e., each data point) would have to be removed and handled separately. A shortcoming of having to remove each pin separately is that this leads to inconsistent data because some pins remain in contact with the liquid growth medium longer than others, therefore the biofilm formed using these systems is not consistent from pin to pin. The lid 90 of the present invention allows the exposure time/growth time of the biofilm to be carefully monitored and controlled by removing the entire lid 90 from the vessel 105 wherein all of the projections and biofilm growing material 300 are affixed to the lid 90. Therefore, the process of removing the lid correlates to removing all of the projections/material from the liquid growth media simultaneously. Thus, the lid 90 promotes uniform formation of biofilm on each of the projections/materials because all of the projections can be removed from the vessel in a single action. The production of uniform biofilms is important to ensure that test results are uniform and accurate. Still further, the apparatus and methods of the present invention allows for high throughput of biofilm formation because a large number of biofilm formation sites may be prepared at once.

The material 300 may include any material in which it is desirable to test the formation of biofilm growth thereupon. For example, it may be desirable to test the growth of biofilms on an aluminum surface, thus the material 300 would include small sections of aluminum tubing disposed upon the projections 130. The material 300 may be retained on the pins by a friction fit. If necessary a bio-compatible adhesive or other means may be utilized to retain the material 300 upon the projections 130.

It shall be understood that although specific references have been made to specific materials regarding the material 300 this shall not be considered limiting in any manner. The material 300 may include any material in which it is desirable to study the growth of biofilm thereon. The material 300 may include aluminum, steel, copper, stainless steel, titanium, silicon, urethane, or similar materials. As shown in FIG. 3, the material 300 may be disposed over more than one projection 130 whereby when the lid 90 is placed on the vessel 105, the ends of the material 300 do not contact a liquid growth medium disposed within the wells 125 of the vessel 105. Furthermore, although the material 300 has been shown as being disposed over the projections forming a u-shape, it is contemplated that the material 300 may be disposed upon the projections in a different manner than that described and shown. It is also contemplated that the material 300 may further include at least one coating in which it is desirable to test the formation of biofilms on the coating. For example, the material 300 may be a catheter which is prepared in the manner described above, in which the catheter has been coated with a coating in which it is desirable to determine the formation of biofilms on the coating. Such coatings may comprise aluminum, stainless steel, silver, copper, hydroxypatite, silicon, latex, urethane, PVC, and ceramic, steel, gold, titanium, polyethylene, and polysilicone. It shall be understood that the coatings listed above are merely exemplary and should not be considered limiting in any manner.

Figure 5:
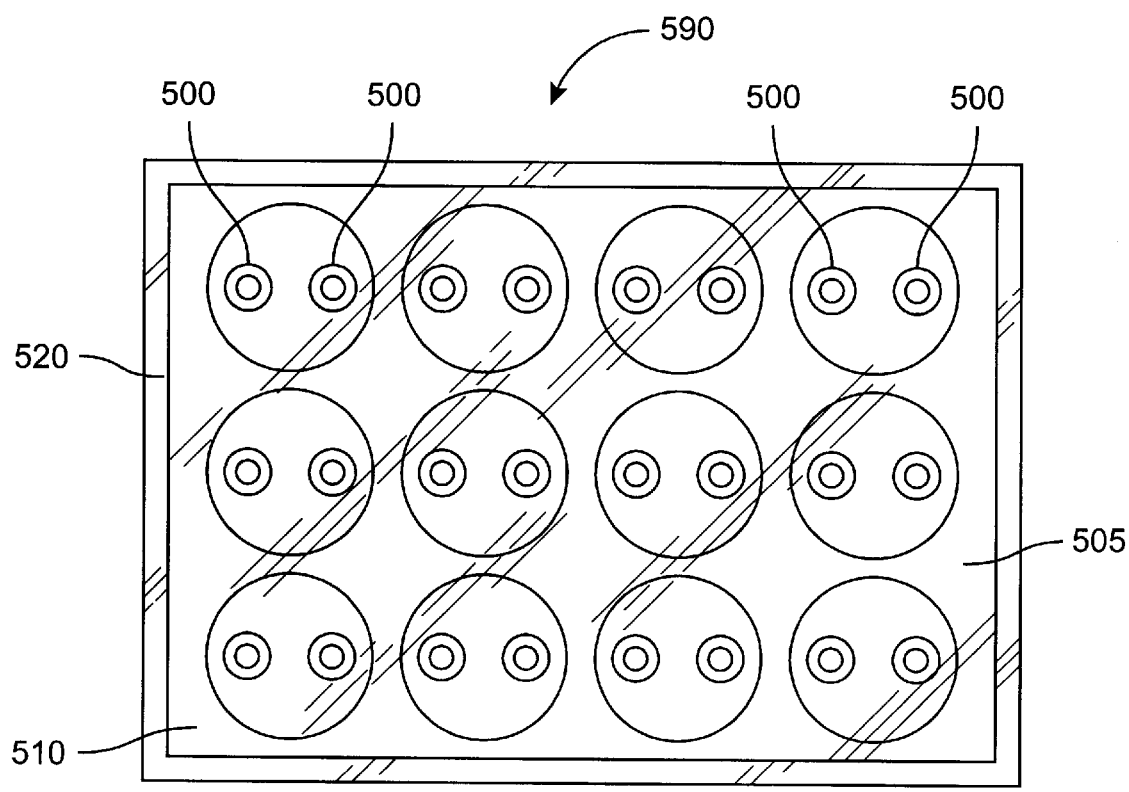
FIG. 5 is a bottom view of an alternative embodiment of the lid of the present invention illustrating a material being attached to a first surface of the lid.
Figure 6:
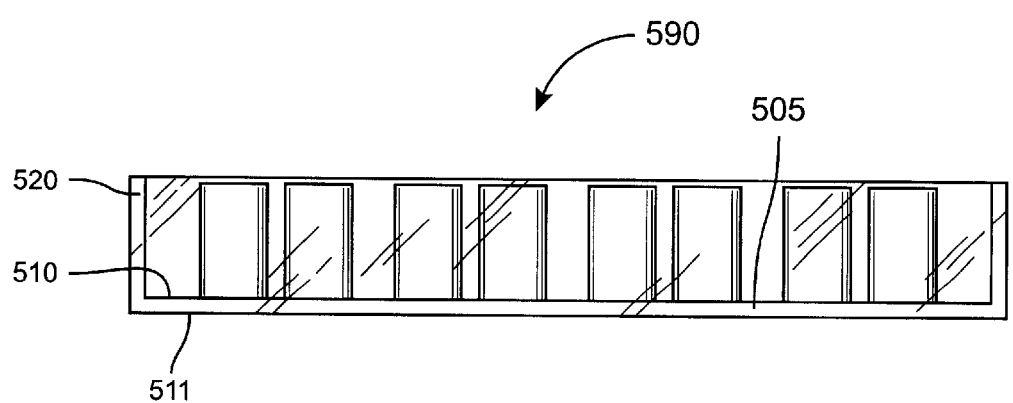
FIG. 6 is a side view of the alternative embodiment of FIG. 5 of the present invention.

Referring now to FIGS. 5 and 6, there is shown an alternative embodiment of the lid 590 of the present invention. The lid 590 includes a plate 505, the plate having a first surface 510 and a second surface 511 (not shown), and walls 520 defining the lid 590. The lid 590 further includes a plurality of elements of biofilm growing material 500. The elements of biofilm growing material 500 may be constructed of materials such as aluminum, copper, stainless steel, or hydroxyapatite. The materials listed above are merely exemplary and should not be considered limiting in any manner.

In addition, the material 300/500 are utilized to model surfaces and devices which may be in contact with a patient during a medical procedure. For example, the hydroxyapatite may be utilized to model a patients tooth, the stainless steel may be utilized to model a medical device such as a scalpel or scissors. The biofilm growing material may be fixedly attached utilizing a bio-compatible glue or bio-compatible process to the projections 530 (not shown). Alternatively, the lid 590 may be formed wherein the biofilm growing materials 500 are integrally formed with the lid 590 during the manufacturing process. In another embodiment, the lid 590 may not contain the projections 530, wherein the bio-compatible material 500 is fixedly attached to the first surface 510 of the lid 590 using a bio-compatible adhesive.

The biofilm growing material 500 may have a generally tubular shape as shown in FIGS. 5 and 6. Alternatively, the biofilm growing material 500 may be formed in any manner, such that the lid 590 may be utilized with a ninety-six well plate or other well plates having different well configurations. As described above, the lid 590 may be formed of any bio-compatible material such as titanium, stainless steel or plastics such as polystyrene and low density polyethylene (LDPE).

Figure 7:
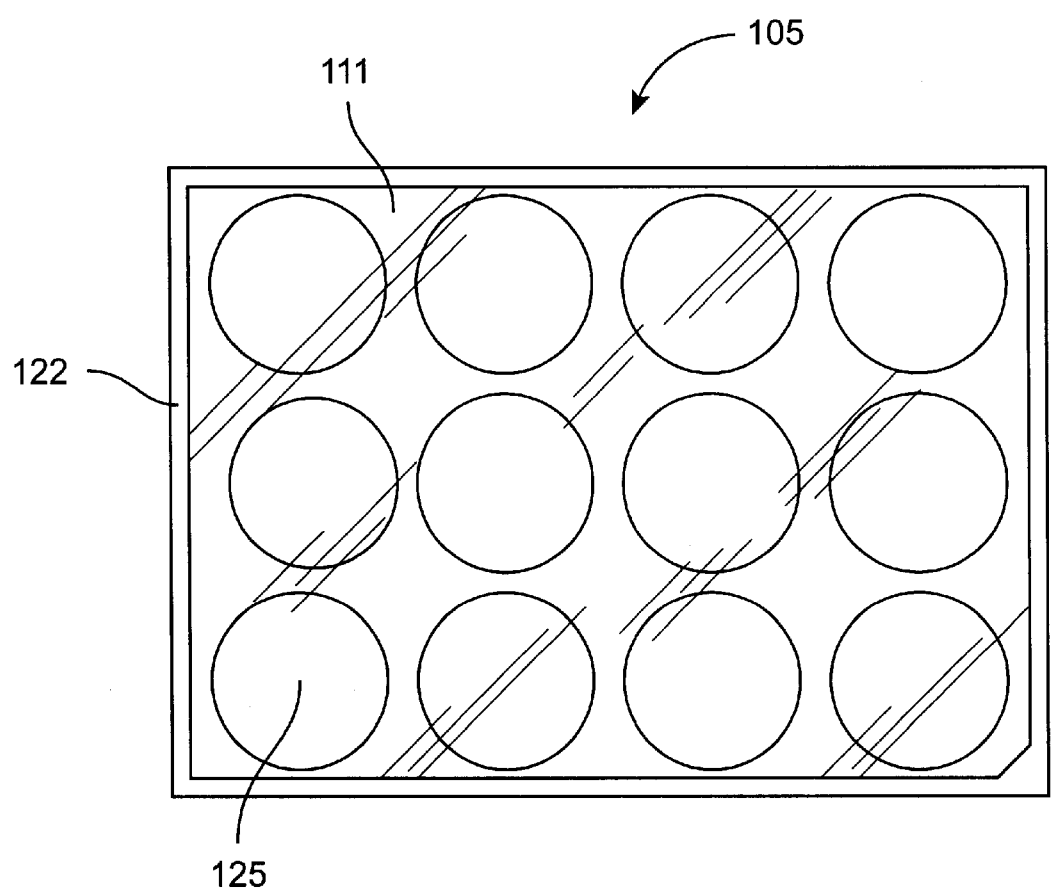
FIG. 7 is a top view of a vessel of the present invention.
Figure 8:
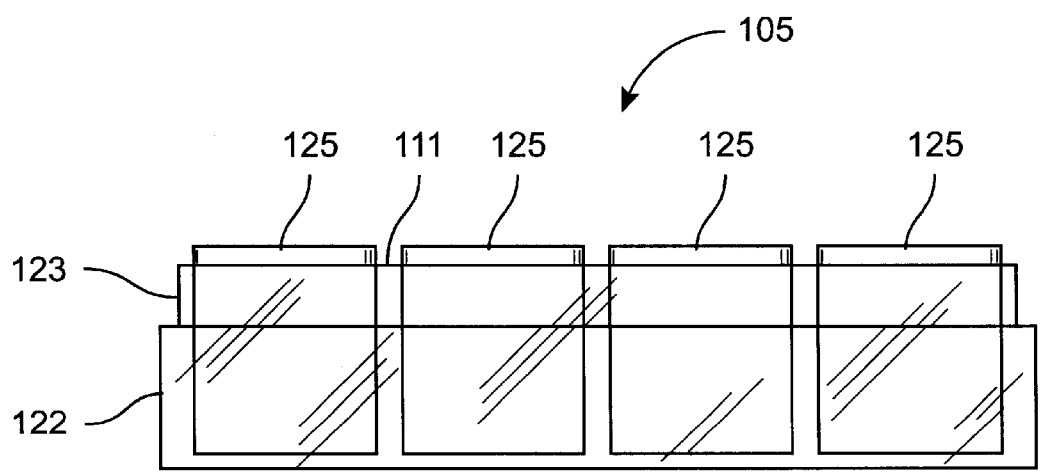
FIG. 8 is a side view of the vessel of the present invention.

Referring now to FIG. 7, there is shown a vessel 105. The vessel 105 includes a first surface 111, sides 122, and a plurality of wells 125. The wells 125 are disposed within the vessel 105 whereby when lid 90 is placed onto the vessel 105 a pair of protrusions are aligned with a bore of each well 125, respectively. As shown in FIG. 8, the vessel 105 contains a protrusion 123 whereby a ledge is formed between the wall 122 and the protrusion 123. The protrusion 123 is adapted to receive the wall 120 of the lids 90,590 as shown in FIG. 2. When the lid 90, 590 is disposed upon the vessel 105 a fluid tight seal is formed between the walls 120 of the lid 90, 590 and the protrusion 123 of the vessel 105. This fluid tight enclosure prevent contamination of the liquid growth medium disposed within the vessel 105. Although the vessel 105 is illustrated as containing 12 wells, it is contemplated that other numbers of wells may be utilized. It shall be understood that the vessel 105 will be chosen such that the number of wells which will correspond to the number of pairs of projection on the lid 90.

The vessel 105 may be formed of a bio-compatible material such as stainless steel or titanium. Preferably the vessel 105 is formed of a bio-compatible plastic such as polyvinylchloride (PVC), polyethylene, low density polyethylene (LDPE), polystyrene, urethane, silicon, delrin, or similar materials. Furthermore, the vessel 105 may be formed having transparent or opaque characteristics thereby allowing a user to view the biofilm formation on the projections 130 or material 300/500.

Figure 9:
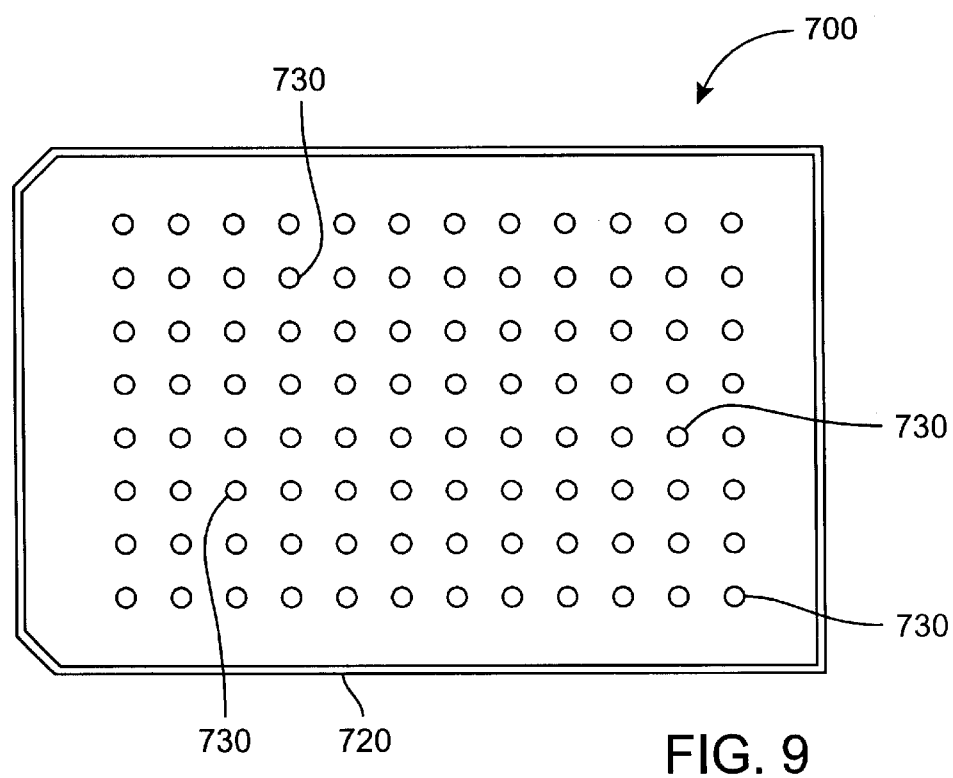
FIG. 9 is a bottom view of a lid configured for use with a 96 well plate or a vessel with channels according to the present invention.
Figure 10:
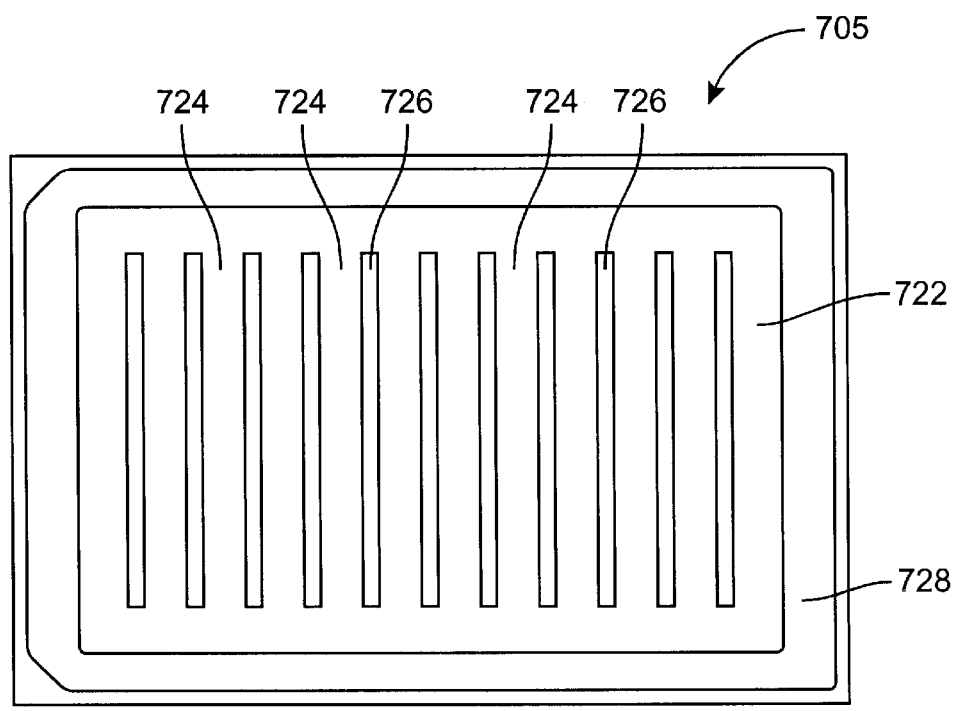
FIG. 10 is a top view of an alternative embodiment of a vessel with channels for use with the methods and apparatuses of the present invention.
Figure 11:
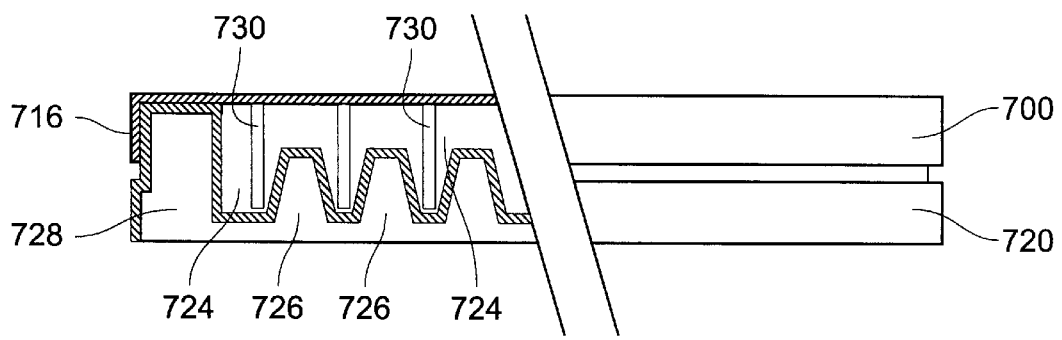
FIG. 11 is a side cross sectional view of the lid of FIG. 10 of the present invention as assembled with the vessel of FIG. 10.
Figure 12:
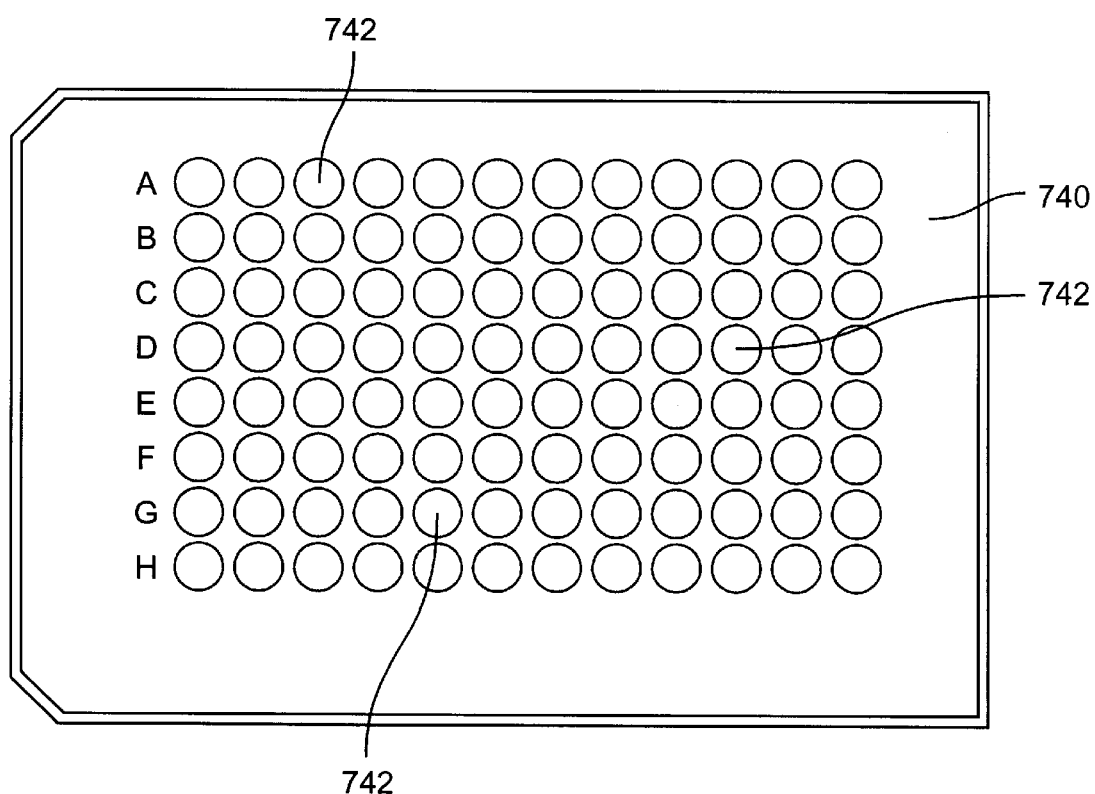
FIG. 12 is a top view of a ninety-six well plate for use with the present invention.

Referring now to FIGS. 9–12, there is shown yet another alternative embodiment of the biofilm growing apparatus of the present invention. As shown more particularly in FIGS. 9–12, the biofilm assay device includes a biofilm lid 700. The lid 700 includes projections 730 extending from a first surface 710 of the lid 700, and walls 720. The projections 730 form biofilm adherent sites to which a biofilm may adhere. The lid 700 may be composed of a bio-compatible plastic or metals such as: polystyrene, polyvinylchloride, polyethylene, stainless steel, titanium, or other suitable bio-compatible materials. The projections 730 may be formed in at least eight rows of at least twelve projections in each row as shown in FIG. 9. In this configuration, the lid 700 may be combined with a commonly available ninety-six well plate as shown in FIG. 12 in order to form a fluid tight container for growing biofilms. Although the projections 730 have been described as being disposed upon the lid 700 having specific geometry, it is contemplated that the projections 730 may be disposed in any manner upon the first surface 710 of the lid 700, such as those methods described above.

Referring now to FIG. 10, there is shown a vessel 705. The vessel 705 includes a liquid holding basin 722, wherein the liquid holding basin 722 is divided into a plurality of channels (troughs) 724 by molded ridges 726. The channels 724 are wide enough to receive the projections 730. There should be at least one channel 724 for each row of projections 730. As described above and illustrated in the drawings the lid 700 and vessel 705 are designed such that the vessel will accept the lid 700 thereby forming a fluid tight seal between the lid and the vessel. The vessel 705 may be utilized with lid 90 to form an assembly for the formation of biofilms, though in a preferred embodiment, vessel 705 is combined with lid 700 to form an assay assembly as shown in FIG. 11.

The projections 130/730 may further be coated with a biofilm growing material, thereby enabling the testing of biofilm growth on various materials. For example, it may be desirable to test the biofilm formation on aluminum or similar metals. Each of the projections 130/730 may be coated with aluminum foil. The projections would be coated by obtaining a sheet of foil, cutting a small one inch squared section of the foil, wrapping the foil around an inoculum loop (approximately 1.5 centimeters in diameter) to form and open ended cylinder. The open ended cylinder may then be fitted onto a single projection 130/730 upon which a drop of cement may be placed to retain the foil onto the projection 130/730. The protruding end of the foil may then be wrapped around the top of the projection 130/730 and the excess cut off. This process may be repeated until a desired number of projections are coated. It shall be understood that the process described above is merely exemplary and should not be considered limiting, other methods may be utilized to coat the projections. For example, the projections 130/730 may be coated utilizing a spray coating process, vapor depositing process, dipping or other similar processes.

Alternatively, it may be desirous to test biofilm growth on other materials. Such a material may be hydroxapatite. The projections 130/730 may be coated with hydroxapatite, by first coating the projection with a bio-compatible adhesive and then placing the projections into a trough containing hydroxapatite crystals and allowing the adhesive to set. The projections 130/730 may then be removed from the hydroxapatite crystals and allowed to sit for a period of time, or until the adhesive has dried. The process may be repeated until the projections are fully coated with hydroxapatite crystals. Additionally, the projections 130/730 may be coated in a similar manner with a different material in which it is desirous to study the biofilm growth thereon.

Figure 13:
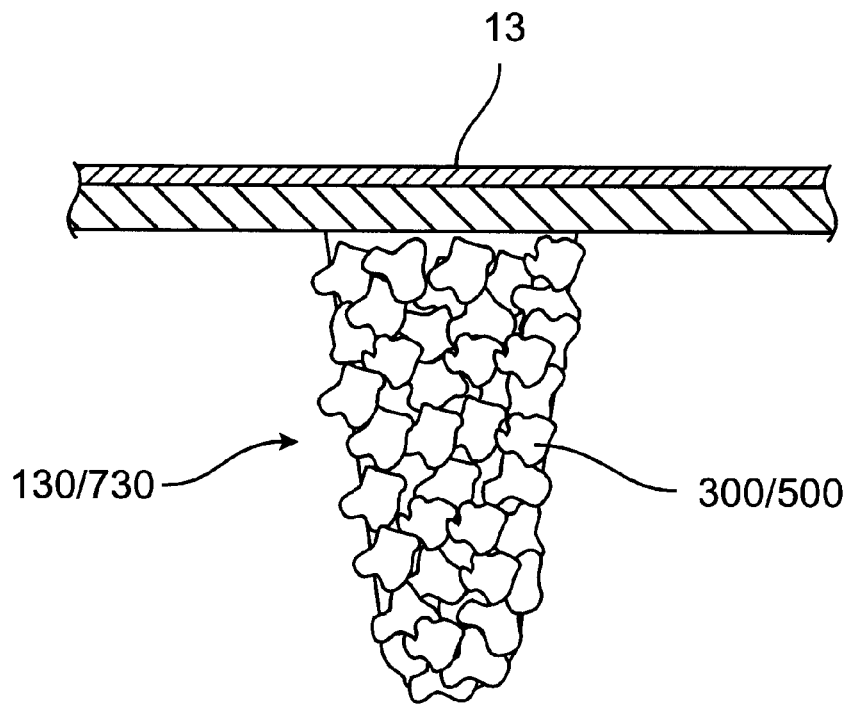
FIG. 13 is a side view of a projection having been coated with a material for testing biofilm formation thereupon.

In one embodiment the projections 730 of lid 700 may be formed having a hollow cross-sectional area. In the case where the projections are formed having a hollow cross-section a sheet of plastic 13 should be disposed over the hollow section as illustrated in FIG. 13. The plastic sheet 13 covering the hollow area of the projections 730 prevents contamination of the assay assembly in instances where projections have been removed from the plate for testing of the biofilm formation thereon. Additionally, as shown in FIG. 13, the projection(s) 130/730 may have a material 300/500 disposed thereupon. The material 300/500 has been disposed upon the projection 130/730 utilizing any one of the methods described above.

As shown in FIGS. 2, 8, and 11, the vessels 105 and 705 serve two important functions for biofilm development. The first function is as a reservoir for the liquid growth medium containing biofilm forming organisms which will form a biofilm on the projections 130/730. The second function of the vessel is to generate a shear force across the projections. The generated shear force allows for optimal biofilm formation on the projections. The biofilm forming organisms may, for example, be bacteria, yeast, or fungi. The fungi may further be filamentous fungi. The shear force developed in the vessels may be generated by a rocking table or a gyrating shaker. The proper device for generating the shear force will be chosen according to which vessel is utilized in the assembly. In the instances where the vessel 105 is being utilized, the use of a gyrating shaker is preferred. The gyrating shaker is preferred because the motions that are produced cause a centrifugal force to be generated in the liquid growth medium. This centrifugal force is necessary because it causes consistent formation of biofilm on the projections or material disposed upon the projections of the lid 90 by causing the liquid growth medium to pass over the projections evenly. An appropriate gyrating shaker may be obtained from New Brunswick Scientific Co. Inc.

Alternatively, if the vessel 705 is utilized in the assay, then it is preferable to utilize a rocking table to generate the necessary shear force. In this embodiment it is preferred to utilize a rocking table because the back and forth motion causes the formation of consistent biofilms on the projections, by causing the liquid growth medium to pass over the projections evenly. An appropriate rocking table that may be utilized with the assay assembly disclosed herein is the Red Rocker available from Hoffer.

Although each embodiment has been described in a preferred embodiment, it is contemplated that either method of providing flow of the liquid growth medium may be utilized for each assembly. It shall be understood that the gyrating shaker is preferably utilized with the vessel 105 because the gyrating shaker generates centrifugal forces in the liquid growth medium, thus causing the liquid growth medium to flow around the projections and/or material disposed within each of the wells. If the rocking table was utilized with the vessel 105, the rocking motion may cause some of the liquid growth medium to contact the un-coated portions of the material disposed within the wells, thereby interfering with the formation of the biofilm on the coated surfaces as described above. Furthermore, because the wells 125 have a generally cylindrical shape, the centrifugal motion is the most efficient motion to use in order to provide laminar flow of the liquid. In addition, the gyrating shaker may be utilized with the alternative embodiment of the present invention in order to provide laminar flow of the liquid growth medium across the plurality of projections and/or material disposed therein, though the biofilm formation may not be uniform across the projection/material as it would be if the rocking table was utilized.

While it is possible to grow biofilm with only one direction of fluid flow, the vessel must be designed so that the fluid may flow into the vessel in one side and out of the vessel in another side, thereby increasing the costs of the device as well as the complexity. By contrast the constant motion and the turbulence that results from the rocking or shaking, and the design of the vessel (i.e., wells, troughs, recesses, or similar geometries) is simple to achieve, and has been found effective to achieve even biofilm growth.

As described herein the projections and the channels should all have substantially the same shape (within manufacturing tolerances) to ensure uniformity of shear flow across the projections during biofilm formation. In addition, all of the uniform channels may be connected so that they share the same liquid nutrient and mixture. It is also contemplated that the channels could be formed to extend from one wall of the vessel to the other wall of the vessel and thereby act in a similar manner to the individual wells of the first vessel 105 wherein the liquid growth medium is disposed within each individual channel or well. With sharing of the same biofilm forming soup and channel/well configuration for all biofilm formation sites, the biofilms formed are considered to be equivalent for the purpose of testing microbial reagents. Therefore, different concentrations of different antimicrobials may be compared to each other without regard to positional variance of the projections. Thus, the biofilms that are produced utilizing the apparatuses described herein are considered to be uniform.

Methods of Use

The present invention provides an apparatus and methods for testing the effects of materials and surface coating on the formation of biofilms. This may be accomplished by placing the lid 90/590, which was colonized with a bacterial biofilm in an incubation vessel into a vessel 105 such as that shown in FIGS. 2, 7, and 8. As described above, the vessel 105 includes a number of wells 125 adapted to receive the projections 130 and the material 300/500 disposed thereupon. A liquid growth medium containing an antibiotic or biocide is disposed within the well 125 of the vessel 105, as described above, the biofilm formed on each of the projections or material 300/500 are considered to be the same, therefore a different microbial reagent should be disposed within different wells 125. By performing the experiment in this manner consistent results may be obtained because the growth conditions on each of the projections or materials in each of the wells will be very similar. Thus contributing to the overall reliability of antimicrobial treatment of the projections or materials of different wells.

Additionally, the process as described above further requires the use of a second vessel, wherein the second vessel does not contain any wells or flow dividers. This plain vessel is required to prevent contamination and also to cover the projections in a low profile manner, thereby allowing a standard ELISA plate reader to be utilized. For each assay two ninety-six well plates will be needed to provide the traditional Minimum Inhibitory Concentration (MIC) and the Minimum Biofilm Eliminating Concentration (MBEC).

EXAMPLES

For each organism a biofilm growth curve should be determined to ensure the biofilm has reached satisfactory proportion to be tested for antibiotic/biocide sensitivity.

The innoculms for use in the present example were prepared by the direct colony suspension method from 18 to 24 hours. *Pseudomas aeruginosa* colonies grown on Tryptic Soy Agar plates and *Streptococcus salivarus* were grown on Blood Algar Plates at 37 degrees centigrade. The *Streptococcus salivarus* colonies were suspended in 3 milliliters of simple salts media and *Pseudomas aeruginosa* colonies were suspended in Tryptic Soy Broth (BDH) to a turbidity of 1.0 MacFarlands Standard. Then 1 milliliter of each suspension was diluted in 29 milliliters of the corresponding liquid media and viable counts of *Pseudomas aeruginosa* were determined on Tryptic Soy Algar and those of *Streptococcus salivarus* obtained on Blood Algar Plates, where the innoculms were $10^5$ for *Pseudomas aeruginosa* and $10^2$ for *Streptococcus salivarus*. Then 25 milliliters of the diluted suspension were added to the vessel of a device as shown in FIG. 11 along with 600 micro-liters of Fetal Calf Serum with all *Streptococcus salivarus innoculms*. Biofilm formation was carried out utilizing a rocking table to generate the required laminar flow at 35 degrees Celsius and at 95 percent humidity.

MBEC and MIC *Streptococcus Salivarus*

After the initiation of Biofilm formation as described above, about four projections 130/730 were removed by breaking them free from the lid from various locations on the lid at 1 through 8 hours and again at 12 hours. The projections were rinsed in 0.9 percent saline, each placed in a separate well in a vessel containing 200 micro-liters of 0.9 percent saline and sonicated for five minutes to disrupt biofilm formation. Viable counts were determined by serial dilutions on Tryptic Soy Agar Plates for the *Pseudomas aeruginosa* biofilms and Blood Algar Plates for *Streptococcus salivarus* biofilms.

Biocides were prepared concurrently with the preparation of the innoculums as described above. The biocides utilized in the testes described herein comprise, Salvon (Zeneca), Kathan (Rohm and Haas), $R_x$ 7816 (Benz). Each of the biocides were prepared in 0.9 percent saline as working solutions of 1.0 percent, 10 parts per million, 100 parts per million, and 1000 parts per million respectively for all planktonic, control surface, and aluminum surface tests. Each of the biocides were prepared 2 hours prior to the test. From each of the working solutions as prepared above, twofold serial dilutions in 0.9 percent saline were made from columns 2 to 11 in a ninety-six well plate. A single column was left as a sterility control and another column was left as a growth control column. When testing the biocides on the biofilm grown on the surface, stock solutions of the biocides were utilized.

After the biofilms had formed on the material to be tested, or on the coated projections, one of each (i.e., one projection or one section of material) were transferred to a challenge plate prepared as described above after being rinsed for at least two minutes in 0.9 percent saline. The challenge plates were covered with a plain vessel and incubated for about 2 hours at 35 degrees Celsius. After the incubation period the cover was removed from the challenge plates and the projection or material was rinsed twice for at least two minutes each time in 0.9 percent saline.

The lid containing the remaining projections or materials was then placed into a second plate containing 200 microliters of Simple Salts Media in each well for *Pseudomas aeruginosa* biofilms and into 200 micro-liters of Mueller Hinton Broth (BDH) in each well for *Streptococcus salivarus* biofilms. The biofilms were then disrupted and viable counts were determined as described above.

The apparatus described herein may also be utilized for testing the effect of antimicrobial materials or surface coatings. That is a lid may be prepared in the manner as described above, though the projections or the material disposed upon the projections may further include an antimicrobial coating. The projections and/or material is placed into a vessel containing a bacteria and a liquid growth medium and allowed to incubate as described above and maintained for a predetermined time to simulate exposure of a surface likely to be involved in biofilm growth. The projections and/or material are then removed from the first vessel and placed into a second vessel wherein the second vessel contains a buffer solution. This method of testing provides a more sensitive test and illustrates larger differences in antimicrobial effect between coatings because the antimicrobial coating has time to take effect on bacteria growth than the presently used tests wherein the bacteria remains in contact with the material or projections during the testing of the antimicrobial reagent.

The apparatus and methods described herein may also be utilized to model devices and materials. For example, if a new catheter for use during a surgical procedure is designed, it may be desirable to test the formation of biofilm growth on the surface of the catheter. Additionally, it may be desirable to test the effects of surface coatings on the catheter and the formation of biofilms on the catheter surface coatings. For example, it may be desirable to form the catheter with a lubricious coating, prior to using the device within a patient it would be desirable to determine if the lubricious coating promotes biofilm formation. Thus, a catheter would be prepared as it would be utilized within the patient's body. Small sections of the catheter would be prepared and disposed upon the projections as shown in FIGS. 3 and 4, thereby allowing the testing of biofilm formation on the catheter. It shall be understood that any material in which it is desirable to test the formation of biofilm growth thereupon could be utilized, for example, cannulas, iv drip line, syringes, needles, stents and other similar devices and products.

Although the methods and procedures have been described above with regard to the apparatus shown in FIGS. 1-2 this shall not be considered limiting. The methods described herein may be utilized with other assay systems available.

While the preferred technique is to reverse flow of the liquid growth medium, the array could have a unidirectional flow of liquid. That is re-circulation of fluid from one end of each vessel to the other end of the vessel, though this would complicate the process greatly due to the increased complexity of the system and the possibility of contamination of the fluid.

It shall be understood that the methods and apparatus described herein shall not be considered limiting. It shall be understood to one skilled in the art that modifications could be made to the invention as described herein without departing from the essence of the invention that is intended to be covered by the scope of the claims that follow.

What is claimed is:

1. A method for growing a plurality of biofilms, said method comprising:
   providing a plurality of biofilm adherent sites;
   providing said biofilm adherent sites with a surface material, wherein said surface material models a surface to be involved in biofilm formation;
   providing a flowing liquid growth medium arranged to flow across said biofilm adherent sites; and
   incubating microorganisms on said biofilm adherent sites in the presence of said liquid growth medium.

2. The method of claim 1, wherein said bacteria is incubated in the form of a biofilm.

3. The method of claim 1, wherein said biofilm adherent sites are coated.

4. The method of claim 3, wherein said coating is chosen from the group consisting of aluminum, stainless steel, silver, copper, hydroxypatite, silicon, latex, urethane, PVC, and ceramic, steel, gold, titanium, polyethylene, and polysilicone.

5. The method of claim 3, wherein said coating is hydroxyapatite, wherein said hydroxyapatite is adhered onto said biofilm adherent site with adhesives.

6. The method of claim 2, wherein said method comprises agitating said liquid growth medium, such that said liquid growth medium flows across said biofilm adherent sites.

7. The method of claim 4, wherein said coating models a body part.

8. The method of claim 4, wherein said coating models a medical device.

9. The method of claim 4, wherein said coating models an industrial site.

10. The method of claim 4, wherein said coating is disposed upon said biofilm adherent sites wherein said biofilm adherent sites are in the form of a projection.

11. The method of claim 1, further comprising exposing said bacteria to a biocide.

12. The method of claim 1, wherein the surface material is a portion of a medical device.

13. The method of claim 12, wherein the medical device is a catheter affixed to the biofilm adherent sites.

14. The method of claim 12, wherein the medical device is a stent affixed to the biofilm adherent sites.

15. The method of claim 1, wherein the flowing motion of the liquid growth medium is provided by a gyrating shaker.

16. A method for testing the effect of materials and surface coatings on the formation of biofilms in a controlled environment, said method including:
    providing a plurality of biofilm adherent sites;
    coating said biofilm adherent sites with a material which acts as a model for a surface to be involved in biofilm formation;
    providing a liquid growth medium arranged to flow across said biofilm adherent sites;
    agitating said liquid growth medium; and
    growing microorganisms on said biofilm adherent sites.

17. The method of claim 16, wherein said coating is chosen from the group consisting of, aluminum, stainless steel, silver, copper, hydroxypatite, silicon, latex, urethane, PVC, and ceramic, steel, gold, titanium, polyethylene, and polysilicone.

18. The method of claim 17, wherein said coating is adhered to said biofilm adherent sites with an adhesive.

19. The method of claim 16, wherein said coating is a catheter.

20. The method of claim 16, wherein said coating is a medical device.

21. The method of claim 20, wherein said medical device is a stent.

22. An apparatus for testing the effect of materials and surface coatings on the formation of biofilms in a controlled environment, said apparatus including:
    a first body having first and second surfaces, wherein said first body further includes a plurality of protrusions extending from said first surface, wherein said protrusions are provided with a material for biofilm growth which models a surface to be involved in biofilm growth; and
    a second body having sides and a bottom defining a vessel, said second body adapted to receive said first body, wherein said second body includes a plurality of depressions adapted to receive the protrusions wherein said depressions are further adapted to receive a fluid.

23. The apparatus of claim 22, wherein said material includes a coating chosen from the group consisting of; aluminum, stainless steel, silver, copper, hydroxypatite, silicon, latex, urethane, PVC, and ceramic, steel, gold, titanium, polyethylene, and polysilicone.

24. The apparatus of claim 22, wherein said material is a coating for promoting biofilm growth.

25. The apparatus of claim 22, wherein said material is a coating for preventing biofilm growth.

26. The apparatus of claim 22, wherein two of said projections retain said material such that said material forms an arch between the two projections.

27. The apparatus of claim 26, wherein said material comprises first and second ends, and two projections are adapted to retain said first and second ends such that said first and second ends are not immersed in the fluid disposed within the vessel.

28. The apparatus of claim 22, wherein said material is a portion of a catheter attached to the projections.

29. The apparatus of claim 28, wherein said material has a tubular cross-section.

30. The apparatus of claim 22, further including means for generating flow across the projections.

31. The apparatus of claim 30, wherein the means to generate flow includes a gyrating shaker.

32. The apparatus of claim 22, further comprising the fluid received within said depressions wherein said fluid comprises a liquid growth medium.

33. The apparatus of claim 22, wherein said projections are configures to be selectively removed from said first body.

34. The apparatus of claim 22, wherein said first body, said vessel and said members are constructed of plastic.

35. The apparatus of claim 22, wherein said material includes a stent disposed upon at least one projection.

36. A method for testing the formation of biofilm growth on a material or surface coating, the method including:
   at least partially covering a plurality of projections in a testing apparatus with a material to be tested for biofilm formation;
   placing the projections into a first vessel containing at least one well, wherein the well includes a liquid growth medium and a biofilm forming organism; and
   removing the projections from the first vessel and placing the projections into a second vessel, wherein the second vessel contains a second medium.

37. The method according to claim 36, wherein the material to be tested is hydroxyapatite.

38. The method according to claim 36, wherein the material to be tested is a medical device.

39. The method according to claim 38, wherein the medical device is a catheter.

40. The method according to claim 36, wherein the material to be tested further includes a coating.

41. The method according to claim 40, wherein the coating is a biofilm inhibiting coating.

42. The method according to claim 36, wherein the coating is chosen from the group consisting of aluminum, stainless steel, silver, copper, hydroxypatite, silicon, latex, urethane, PVC, and ceramic, steel, gold, titanium, polyethylene, and polysilicone.

43. The method according to claim 36, wherein the material is disposed between at least two projections, whereby first and second ends of the material do not contact the liquid growth medium.

44. The method according to claim 36, wherein the liquid growth medium further includes a bacteria.

45. The method according to claim 36, wherein the second medium is a buffer solution.

46. The method according to claim 36, wherein the second medium is a growth medium.

47. A device for testing the formation of bioflim on various materials or surface coatings, the device comprising:
   a lid, the lid having a first and second surface and sides projecting from and defining the first surface wherein a plurality of apertures are formed through the first and second surface;
   a plurality of projections disposed within the plurality of apertures and extending from the first surface of the lid; and
   a protective sheet disposed over the second surface of the lid, wherein the protective sheet provides a fluid tight seal between the projections and the apertures.

48. The device according to claim 47, wherein the plurality of projections are constructed of a different material than said lid.

49. The device according to claim 48, wherein at least one of the projections is constructed of a material different than the other projections.

50. The device according to claim 48, wherein the projection includes a first end and a second end, the second end configured to be received and retained by the second surface of the lid.

51. The device according to claim 47, wherein the protective sheet provides a fluid tight seal around the aperture wherein at least one projection is removed from the lid.

52. The device according to claim 47, wherein the projections further include a coating disposed thereon.

53. The device according to claim 47, wherein the projections comprise portions of at least one implantable material.

54. The device according to claim 53, wherein at least two of the implatable material portions are coated with different coatings.

55. The device according to claim 47, wherein the plurality of wells are configured to receive a liquid growth medium therein.

56. The device according to claim 55, wherein the liquid growth medium includes a microorganism disposed therein.

57. A device for testing the formation of biofilms, the device comprising:
   a lid, the lid including a first and second surface, sides and a plurality of projections extending from the first surface, wherein the protrusions are affixed at one end to the second surface and pass through apertures formed through the first and second surfaces;
   a protective sheet disposed over the second surface of the lid, wherein the protective sheet provides a fluid tight seal between the projections and the apertures; and
   a vessel, the vessel configured to receive the lid in a fluid tight configuration, the vessel further including a plurality of wells.

58. The device according to claim 57, wherein at least two of the projections are constructed of different materials.

59. The device according to claim 58, wherein the projections are constructed of a material different than the lid.

60. The device according to claim 57, wherein the wells are configured to receive a liquid growth medium.

61. The device according to claim 60, wherein the liquid growth medium includes at least one microorganism.

62. The device according to claim 57, wherein the each of the wells are in fluid communication with each other.

63. The device according to claim 57, wherein the projections are detachably attached to the lid.

64. The device according to claim 57, wherein the at least one projection is coated with a first coating.

65. The device according to claim 64, wherein a second projection is coated with a second coating, wherein the first and second coatings are different.

66. The device according to claim 57, wherein the protective sheet provides a fluid tight seal around the aperture wherein at least one projection is removed from the lid.

67. The method of claim 1, wherein said microorganisms are a bacteria.

68. The method of claim 16, wherein said microorganisms are a bacteria.

69. A method for growing a plurality of biofilms, said method comprising:
   providing a plurality of biofilm adherent sites;
   coating said biofilm adherent sites with a surface material, wherein said surface material models a surface to be involved in biofilm formation;
   providing a flowing liquid growth medium arranged to flow across said surface material; and
   incubating microorganisms on said surface material in the presence of said liquid growth medium.

70. The method of claim 69, wherein said microorganisms are a bacteria.

71. The method of claim 69, wherein said microorganisms are incubated in the form of a biofilm.

72. The method of claim 69, wherein said biofilm adherent sites are coated.

73. The method of claim 72, wherein said coating is chosen from the group consisting of aluminum, stainless steel, silver, copper, hydroxypatite, silicon, latex, urethane, PVC, and ceramic, steel, gold, titanium, polyethylene, and polysilicone.

74. The method of claim 72, wherein said coating models a body part.

75. The method of claim 72, wherein said coating models a medical device.

76. The method of claim 72, wherein said coating models an industrial site.

* * * * *